United States Patent [19]

Savory et al.

[11] 4,299,617
[45] Nov. 10, 1981

[54] METHOD AND COMPOSITION TO INCREASE THE SUGAR CONTENT OF SUGAR CANE

[75] Inventors: Brian Savory, St. Germain; Jacques Desmoras, Orly, both of France

[73] Assignee: Rhone-Poulenc Agrochimie, Lyons, France

[21] Appl. No.: 887,329

[22] Filed: Mar. 16, 1978

Related U.S. Application Data

[63] Continuation of Ser. No. 640,859, Dec. 15, 1975, abandoned.

[30] Foreign Application Priority Data

Nov. 18, 1975 [FR] France ................. 75 35739

[51] Int. Cl.³ ............ A01N 37/38; A01N 37/18
[52] U.S. Cl. ..................... 71/109; 71/86; 71/116; 71/118
[58] Field of Search ............ 71/116, 109, 118

[56] References Cited

U.S. PATENT DOCUMENTS

| | | | |
|---|---|---|---|
| 2,927,940 | 3/1960 | Metivier et al. | 71/116 |
| 3,074,791 | 1/1963 | Scoles | 71/109 |
| 3,087,805 | 4/1963 | Metivier | 71/116 |
| 3,245,775 | 4/1966 | Pfeiffer | 71/116 |

OTHER PUBLICATIONS

Beauchamp, "Experiments to Increase the Sugar, etc.," (1952), CA 46, p. 11725, (1952).
Nickell et al., "Effects of Chemicals on Ripening, etc.," (1965) *Haw. Sugar Technol.*, pp. 152–163, (1965).
Tokuoka et al., "The Fertilizer Effect, etc.," (1940), CA 34, pp. 7513–7514, (1940).

*Primary Examiner*—Glennon H. Hollrah
*Attorney, Agent, or Firm*—Browdy and Neimark

[57] ABSTRACT

Sugar content of sugar cane is increased by treating the growing cane with

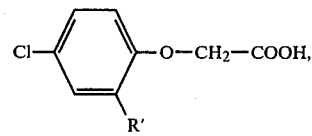

wherein R' is CHO or CH₂OH.

9 Claims, No Drawings

METHOD AND COMPOSITION TO INCREASE THE SUGAR CONTENT OF SUGAR CANE

This is a continuation, of application Ser. No. 640,859 filed Dec. 15, 1975 now abandoned.

FIELD OF THE INVENTION

This invention relates to chemical ripeners for sugar cane. It also relates to a method of treatment of sugar cane in order to increase the sugar content.

BACKGROUND OF THE INVENTION

World hunger is well known to be a problem of extreme importance and is expected to become even more serious in years to come. Among possible solutions which, at present, are helping to solve the problem, are the use of chemical pesticides which prevent agricultural crops from being decimated by parasitical insects or fungi, or strangled by weeds.

It is also known that so-called growth regulators can be used to encourage plant development and increase the potential harvest. In fact, the term "growth regulator" covers an immense number of possible practical functions, which differ fundamentally from each other, such as: to facilitate or inhibit fruit or leaf fall, to avoid or simplify the pruning of fruit trees, to combat "lodging" of cereals, to produce more attractive ornamental plants that are more bushy or more floriferous, etc. Indeed, to call a product a growth regulator is an insufficient indication for the use unless it is completed by more precise information on the conditions under which the "regulator" is to be applied and the crops on which it may be used.

Thus the French Pat. Nos. 1,186,520 filed on Nov. 18, 1957 and No. 1,195,448 filed on Apr. 28, 1958 by Rhone-Poulenc Company describe the compounds of formula

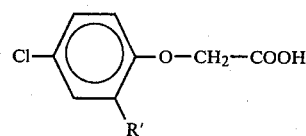

(I)

in which R' represents a CHO or CH$_2$OH radical and Z represents a OH radical, alkyloxy or amino which may be substituted by one or two alkyl radicals. These compounds are presented as growth substances active notably in the formation of new organs (roots) and in the formation of parthenocarpic fruit.

It is also known that certain chemicals can be used to increase the sugar content of sugar cane. Among these products, may be mentioned glyphosine, the chemical structure of which is given below:

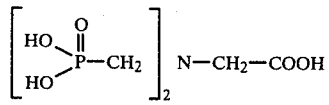

Its use on sugar cane is described in the Dutch patent application No. 6,915,811 of Oct. 21, 1968.

Glyphosine is the only product at present registered for this usage; however, it has the disadvantage of inhibiting the growth of the plant which often considerably restricts the yield increase provoked by its use. This is especially noticeable in regions where the vegetative cycle of the crop is short. Therefore, the need to develop a product which gives a good increase in sugar content of sugar cane with a significant increase in the sugar obtained as an end-product still remains a serious economic problem.

SUMMARY OF THE INVENTION

In accordance with the present invention it has now been determined that the use of compounds corresponding to formula (I) mentioned above, enables the sugar content of sugar cane to be increased in a remarkable and completely unexpected way.

The present invention thus relates to compounds for the treatment of sugar cane in order to increase the sugar content, the compounds being characterized as containing at least one active ingredient of the general formula:

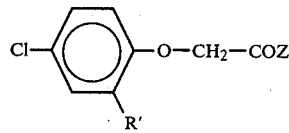

(2)

in which R' represents a CHO or CH$_2$OH radical, or a derivated ester, amide, metal salt, or amine salt of these acids.

This invention also relates to the treatment of sugar cane designed to increase its sugar content, wherein the plant is treated during the growing period with an active quantity of a compound containing at least one active ingredient corresponding to the above formula, or one of its aforementioned derivatives.

DETAILED DESCRIPTION OF EMBODIMENTS

By the expressions "derivative" or "derivated ester, amide, metal salt or amine salt", what is meant is all the salt or esterified forms in which this type of compound is normally used, belonging to the family known as phytohormones which has been known for its herbicidal properties for many years.

Traditionally this kind of compounds is used under one of the following forms:
the acid itself,
its metal salts, namely alkali and alkaline-earth salts, more specifically sodium, potassium and ammonium salts,
its amine salts obtained by reaction of the acid on the primary, secondary or tertiary, optionally substituted most frequently by alkyl and/or hydroxyalkyl radicals. As examples, there may be mentioned the mono-, di- or trimethyl (or alkyl) amines and the higher alkyl homolog optionally substituted by at least one hydroxyl group, the long chain amines such as fatty amines that give hydro- or liposoluble salts or metallic salt or amine salt mixtures.
its alkylesters, namely methyl-, ethyl-, butyl esters, their higher homologes or hydroxyalkyl esters such as butylglycol ester,
its optionally substituted amides.

On a biological level, these different forms all behave in an identical or similar fashion; on the other hand, each one may, under certain conditions, present a specific advantage as regards volatility, penetration into the plant, or phytotoxicity, and therefore the convenience of formulation and other practical considerations will govern the choice of one form rather than another. It is understood that this invention covers in a general way all the usual forms of use of the acids and derivatives defined above, and that the list of derivatives given is only indicative and exemplary.

In order to illustrate the invention more clearly, a few formulations are set forth which are usable in practice and which include one or other of the derivatives previously defined:

| Formulation No. 1 | | |
|---|---|---|
| 2-formyl 4-chlorophenoxyacetic acid | | 102 g |
| soda N | | 466 cc |
| urea | | 150 g |
| adjuvants NPT 10[a] | | 50 g |
| DOS 75[b] | | 3.4 g |
| water | q.s.p. | 1000 cc |
| Formulation No. 2 | | |
| 2-hydroxymethyl 4-chlorophenoxyacetic acid | | 20.5 g |
| soda N | | 92 cc |
| urea | | 25 g |
| NPT 10[a] | | 10 g |
| water | q.s.p. | 1000 cc |
| Formulation No. 3 | | |
| 2-hydroxymethyl 4-chloro phenoxyacetic acid | | 102 g |
| dimethylamine 40% | | 56.8 g |
| urea | | 150 g |
| DOS 75[b] | | 3.4 g |
| water | q.s.p. | 1000 cc |
| Formulation No. 4 | | |
| 2-hydroxymethyl 4-chloro phenoxyacetic acid | | 102 g |
| triethanolamine | | 102 g |
| DOS 75[b] | | 6.6 g |
| cyclohexanone | | 100 g |
| water | q.w.p. | 1000 cc |
| Formulation No. 5 | | |
| 2-formyl 4-chlorophenoxyacetic acid | | 102 g |
| triethylamine | | 51 g |
| urea | | 150 g |
| NTP 10[a] | | 50 g |
| DOS 75[b] | | 3.4 g |
| Formulation No. 6 | | |
| 2-formyl 4-chloro phenoxyacetic acid isoctylic ester | | 160 g |
| cemulsol NP' 1064[c] | | 50 g |
| CA DBS[d] 65% | | 30 g |
| Xylene | q.s.p. | 1000 cc |
| Formulation No. 7 | | |
| 2-hydroxymethyl 4-chloro phenoxyacetic acid ethylic ester | | 120 g |
| cemulsol NP' 1064[c] | | 60 g |
| Ca DBS[d] 65% | | 20 g |
| water | q.s.p. | 1000 cc |
| Formulation No. 8 | | |
| 2-formyl 4-chloro phenoxyacetic acid | | 50 g |
| Talc | q.s.p. | 1000 g |
| Formulation No. 9 | | |
| 2-formyl 4-chloro phenoxyacetic acid potassium ester | | 133 g |
| soda laurylsulfate | | 12 g |
| crushed urea | q.s.p. | 1000 g |
| Formulation No. 10 | | |
| 2-hydroxymethyl 4-chloro phenoxyacetic acid | | 20 g |
| scurol O[e] | | 10 g |
| formamide 1 vol | | |
| cyclohexanol 1 vol | q.s.p. | 1000 g |
| Formulation No. 11 | | |
| 2-hydroxymethyl 4-chloro phenoxyactic acid | | 2.5 g |
| methylic alcohol/distilled water 50/50 | q.s.p. | 1000 cc |

[a]NTP 10 = nonylphenol with 10 ethylene oxide moles
[b]DOS 75 = dioctylsulfosuccinate
[c]non ionic emulsifier: condensate with 10 ethylene oxide moles and nonylphenol
[d]dodecylbenzene sulfornic acid calcium salt
[e]octylphenol with 10 ethylene oxide moles.

The remarkable properties of the compounds of the invention have been demonstrated in trials carried out both in the greenhouse and outdoors under the conditions described in the following examples. All the trials described in the examples were carried out with formulation No. 1 defined above, but additional and more restricted trials have shown that the various other formulations described gave very similar results:

EXAMPLE I

Greenhouse Trials

The product to be tested was sprayed on young sugar cane plants that were about 45 cm high having ten leaves. The formulation initially prepared was diluted in water until sufficient volume was obtained to give a spray of about 200 l/ha. Sixteen plants were used for each trial and untreated checks were included in the experiments. Two, four, seven and ten weeks after treatment, the amount of sucrose in the juice extracted and the purity of the juice was measured, each time by sampling 4 plants in the trial plot.

The results were obtained as follows:

| | % of sucrose in the juice after "n" weeks | | | | Purity of juice in % after "N" weeks | | | |
|---|---|---|---|---|---|---|---|---|
| N = | 2 | 4 | 7 | 10 | 2 | 4 | 7 | 10 |
| Glyphosine 3 kg/ha normal rate of use | 3.0 | 4.1 | 6.3 | 10.0 | 31 | 32 | 43 | 60 |
| Product according to the invention - Formulation No. 1 at 1 kg/ha | 2.5 | 3.6 | 10.1 | 12.1 | 32 | 40 | 65 | 77 |
| Untreated check | 0.5 | 2.5 | 7.4 | 9.7 | 19 | 15 | 54 | 62 |

These results show that, both as regards the sugar content in the juice extracted and also as regards the purity of this juice, these two factors naturally being taken into account in evaluating the final result, the product according to the invention gives remarkable results which are greatly superior to those obtained with the best product known at present. This is despite the fact that the latter (Glyphosine) was used in these comparative trials at a much higher rate.

As regards the size and the weight of the harvested canes, the results obtained with the product of the present invention were virtually equivalent to those obtained with the untreated check, which means that the application of the product did not inhibit the growth of the cane. On the other hand, growth of the canes treated with glyphosine was practically brought to a halt, and the total weight of the canes harvested after ten weeks was only a quarter of that of the untreated canes.

EXAMPLE 2

In this case, outdoor trials were conducted in order to demonstrate the actual increase in utilizable sugar under practical conditions of application. In all the trials carried out on different varieties of sugar cane, under different soil and climatic conditions, the results obtained gave yield increases ranging from 10 to 25%, averaging around 15%.

Thus, in a trial carried out on the sugar cane variety No. 65.69, the results obtained were as follows (given in metric tons/ha of utilizable sugar):

| Check | 8.3 t/ha |
|---|---|

| -continued | |
|---|---|
| Glyphosine at 4.5 kg/ha | 8.4 t/ha |
| Product according to the invention at 2.2 kg/ha | 10.4 t/ha | i.e. an increase of 25% over the check.

In this last test the sugar cane was harvested 4 weeks after the treatment.

Another trial was effected on a plantation of two year old plants of the variety 50 7209 and the sugar canes were harvested 8 weeks after the treatment. The quantity of utilizable sugar was the following:

| product according to the invention at 4.5 kg/ha | 46.2 tons/ha |
|---|---|
| check | 42.0 tons/ha |

All the results given above relate to trials carried out with compounds of the formula (2) where R′=CHO. Virtually equivalent results were obtained, although in general a little less consistently good, where R′=CH$_2$OH.

Among the specific quantities of these compounds, it should be noted that the increase in sugar content of the sugar cane was regular from application to harvest, and also that the products of the present invention applied in no way inhibited the growth of the plant. It is therefore possible to envisage giving very early treatments while the cane is still young and a tractor can still be driven through the plantation. This is not the case with glyphosine-type products, which must be applied using hand operated sprayers or by air, the latter of which is obviously more expensive and can moreover only be utilized on sufficiently large plantations. Air spraying cannot be used for small plantations and is generally more expensive than tractor spraying unless the area to be treated is very large.

As far as can presently be judged from trials carried out to date, the most favorable period for application seems to run from the fourth to the fifteenth week before the date set for harvest, but earlier applications seem to be possible.

Under practical conditions of application, the product may be used at rates ranging from 1 to 6 kg/ha, and the best results were obtained at rates of between 2 and 4 kg/ha.

Of course, the product may if necessary be formulated according to the traditional techniques of the pesticide industry: the formulation used will depend on the physico-chemical characteristics of the active ingredient used and on the practical conditions of use. Thus, ready-to-use formulations (liquid or solid) may be utilized or formulations to be diluted in water or in a suitable dilutant before use.

Among solid formulations, there may be used powders for dusting, wettable powders to be diluted in water, and micro-granules. Among liquid formations, solutions—aqueous, organic or mixed solutions—emulsifiable concentrates, pastes, flowable or other formulations may be used.

All these formulations generally contain, as well as the active ingredient, carriers, diluents or solvents and various formulation adjuvants such as tension-active products such as detergents or surfactants, antifoaming agents, antilumping agents, adhesives, stabilizers, colorants, antifreezing agents, corrosion inhibitors, etc. to improve the quality of the formulation and the product's adhesion to or penetration into the plant.

Among the adjuvants used in connection with this invention, it has been found that urea plays a particularly favorable role and contributes effectively to the quality of the results obtained.

The concentration of active ingredient in the formulations used greatly depends on the type of the formulation. In the case of powders for dusting, concentrations of between 0.5 and 20% and preferably between 2 and 10% should be most commonly used. In the case of formulations to be diluted before use, the concentration of active ingredient may vary between 5 and 95%, but concentrations of from 10 and 60% are those most frequently found.

It will be obvious to those skilled in the art that various changes may be made without departing from the scope of the invention and the invention is not to be considered limited to what is described in the specification.

What is claimed is:

1. A process for treating sugar cane to increase the sugar content thereof, comprising contacting the sugar cane between the fourth and the fifteenth week before its harvest with an active, non-toxic quantity sufficient to increase sugar content of a compound of the formula

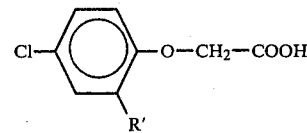

wherein:
R′ is CHO or CH$_2$OH; or a sugar-cane-ripening-effective derivated ester, amide, metal or amine salt thereof.

2. A process according to claim 1, in which the active quantity of active ingredient ranges between 1 and 6 kg/ha.

3. A process according to claim 1, in which the active ingredient is used in acid form.

4. A process according to claim 1, in which the active ingredient is used in the form of a metal salt.

5. A process according to claim 4, in which the metal salt is a sodium, potassium or ammonium salt.

6. A process according to claim 1, in which the active ingredient is used in the form of an amine salt.

7. A process according to claim 1, in which the active ingredient is used in ester form.

8. A process according to claim 1, in which the active ingredient is used in amide form.

9. A process according to claim 1, in which urea is present with said compound.

* * * * *